(12) United States Patent
Trump (10) Patent No.: US 7,976,794 B2
(45) Date of Patent: Jul. 12, 2011

(54) POSITIONING DEVICE FOR THE POSITIONING OF PIPETTES (75) Inventor: Martin Trump, Pforzheim (DE)

(73) Assignee: Stratec Biomedical Systems AG (DE)

( * ) Notice: Subject to any disclaimer, the term of this patent is extended or adjusted under 35 U.S.C. 154(b) by 770 days.

(21) Appl. No.: 11/781,774

(22) Filed: Jul. 23, 2007

(65) Prior Publication Data
US 2008/0019878 A1    Jan. 24, 2008

(30) Foreign Application Priority Data

Jul. 21, 2006 (DE) .................. 10 2006 034 245

(51) Int. Cl.
B01L 3/02 (2006.01)
(52) U.S. Cl. .......... 422/501; 422/63; 422/509; 422/500; 422/81; 222/52; 222/56; 222/71; 222/74
(58) Field of Classification Search .............. 422/63, 422/68.1, 99, 100, 65, 81, 101, 102, 64, 131, 422/135, 134, 923; 73/864.16, 864.25, 863.31, 73/863.32, 864.17; 222/52, 53, 56, 63, 257
See application file for complete search history.

(56) References Cited

U.S. PATENT DOCUMENTS

| 4,679,446 | A |   | 7/1987  | Sheehan et al.          |
|-----------|---|---|---------|-------------------------|
| 5,306,510 | A | * | 4/1994  | Meltzer ......... 422/100 |
| 5,971,007 | A | * | 10/1999 | Harcourt et al. .... 137/246.22 |
| 6,869,571 | B2| * | 3/2005  | Ingenhoven et al. .... 422/100 |
| 2001/0027269 | A1 |   | 10/2001 | Tanaka |
| 2004/0050866 | A1 |   | 3/2004  | Ingenhoven et al. |
| 2004/0076550 | A1 | * | 4/2004  | Ruedisser et al. ........... 422/100 |
| 2004/0094575 | A1 |   | 5/2004  | Toi et al. |
| 2004/0159675 | A1 |   | 8/2004  | Nishino |
| 2006/0127281 | A1 | * | 6/2006  | Bjornson et al. ........... 422/100 |

FOREIGN PATENT DOCUMENTS

| DE | 10351407 A1 | 6/2004 |
| EP | 0311440 A2 | 4/1989 |
| EP | 763772 A | 6/1992 |
| EP | 1477815 A1 | 11/2004 |
| EP | 1652583 A1 | 5/2006 |
| FR | 2434937 A1 | 3/1980 |
| JP | 07063772 A | 3/1995 |
| WO | 88/05541 A1 | 7/1988 |
| WO | 91/16675 A1 | 10/1991 |
| WO | 02/059626 A1 | 8/2002 |
| WO | 02/089981 A2 | 11/2002 |
| WO | 2005/010383 A1 | 2/2005 |

* cited by examiner

Primary Examiner — In Suk Bullock
Assistant Examiner — Sharon Pregler
(74) Attorney, Agent, or Firm — Cantor Colburn LLP (57) ABSTRACT A positioning device is provided for positioning pipettes in medical-technical applications including at least one pipetting apparatus with at least one pipette as well as several drive units for positioning a pipette tip and for moving it over a working area and transversely to a working area, a sliding carriage that is moveable transversely to the working area supports the pipette, at least one pump drive with at least one pump and at least one pump chamber is provided for aspirating or dispensing a medium, such that by providing the at least one pump drive with pump and at least one pump chamber integrated in the sliding carriage that is moveable transversely to the working area, the design of the positioning device becomes compact and precise pipetting is achieved.

19 Claims, 7 Drawing Sheets

POSITIONING DEVICE FOR THE POSITIONING OF PIPETTES

CROSS REFERENCE TO RELATED APPLICATIONS

The present application claims priority from German patent 10 2006 034 245.3, filed on Jul. 21, 2006, the disclosure contents of which are herewith also expressly made the object of the present invention.

TECHNICAL FIELD OF THE INVENTION

The invention relates to a positioning device for positioning pipettes or respectively pipetting tips, more especially for the aspirating and/or dispensing of media in medical-technical applications in accordance with the preamble of claim 1.

BRIEF DESCRIPTION OF RELATED ART

DE 691 26 690 T2 and the associated EP 0 478 753 B1 make known an automated molecular biology laboratory, in which a multiple-axis positioning device is used. The Cartesian robot that is used for positioning with a plurality of sliding carriages is described in EP 0 478 753 B1, column 13, line 18 to column 16, line 12. A third sliding carriage controlled via a toothed rack is displaceable in the vertical direction on two horizontally moveable sliding carriages that are displaceable in the X and Y direction. According to FIGS. 3A to 3E in this document, a needle module is mounted in a spring-loaded manner in a bore of the toothed rack so as to be displaceable. A non-conducting polymer hose leads from the needle tip to the pumps that are disposed on the left-hand side in FIG. 1 externally of the sliding carriage (EP 0 478 753 B1, column 9, lines 22 to 39), which means that additional expenditure is necessary for cabling and connecting the hose to the pumps.

DE 198 47 869 A1 makes known the use of micro pumps in conjunction with pipettes. The drawing shows a separation between pipette and pumps and the precise position of the mounting of the pumps remains open. An additional disadvantage of using the micro pumps is that they do not work accurately enough for the present application.

EP 0 246 632 B1 shows a pipetting device that includes an automatic mechanism for exchanging the pipetting tips. According to claim 1, a device for supplying air to the bottom end of the pipette part and an outlet device are provided, it being possible to supply the outlet tip with air or to aspire air out of the outlet tip. This line to the pump or supply line 17, however, in FIG. 5(a) leads away from the sliding carriage, which means that the pump is not integrated in the pump.

A block with pipettes is displaced in an XY system according to U.S. Pat. No. 5,306,510 A, FIG. 1. According to FIG. 2, setting motors for adjusting the pipette tips are disposed by means of an assembly plate 50. According to column 8, lines 42 to 54 the pump arrangement is not shown in detail, and the pump chamber is secured to the arm, which can be moved up and down. According to column 11, lines 6 to 7, however, the pumps are disposed externally of the XY axis frame.

WO 2005/010383 A1 makes known a three-sided bearing arrangement with initial spring biasing, which enables a profile and also a toothed rack profile to be positioned and arranged in bearings in a precise manner. The three-sided bearing arrangement obviates the need for braking mechanisms in the currentless state. Also, on account of the spring-loading, the system is accommodated in a play-free manner and this results in optimized pipetting quality.

BRIEF SUMMARY OF THE INVENTION

Proceeding from this state of the art, invention enables precise pipetting by means of a compact design of the positioning device.

In this achievement the sliding carriage used transversely to the working area is at the same time employed to accommodate the pipetting apparatus, above all the pump drive and the pump chambers being accommodated by and integrated in the sliding carriage. This means that there is no need for hose connections and externally situated pumps and valves. Since there is no longer a need for hose connections that are conventional in the state of the art and are expensive and time-consumimg to lay and conduct, such a design facilitates integration of the system. The reduction in the number of the said connections and lines also makes a contribution to increased precision. The dead volume between the pump and the pipetting needle is decisive for the precision of each pipetting system. Through the integration of the pump in the sliding carriage, the dead volume of several milliliters—(as is the case in conventional pipetting systems where hose lengths are at least two meters and an inside diameter is 1.5 mm where the said dead volume can rapidly amount to in excess of three milliliters)—is reduced to clearly less than one milliliter substantially through the connecting bore in the valve disk.

A plurality of pump chambers and/or a plurality of pumps with different volumes are preferably integrated in the sliding carriage. This means that, on the one hand, the useful pipetting volume range can be extended, and, at the same time, as long as there is a plurality of pumps, the suitable pump can be selected for the desired pipetting volume. Consequently, this allows optimized pipetting precision over a large volume range. To do this, the device has not had to be designed for the largest possible pipetting volume and this results in greater precision in particular with smaller volumes.

Where required, the sliding carriage that is moveable transversely, preferably at right angles to the working area is formed by a profiled rail, which initially through its form counteracts any rotation. The form of the profile achieves a greater degree of integration by it being possible to dispose components internally of the said profile. At the same time, the profile allows to have the desired arrangement of three sliding bearing guides as well as the accommodation of a cable duct.

Multiple needle arrangements can also be produced in a simple manner. Identical modular units are used and they merely have to be coupled to one another. The selected geometry of the profiled rail produces a fixed spreading without fine adjustments being necessary. If the systems are also provided with a Y sliding carriage, which includes both Z drive and Y drive for example via a spindle nut, autonomous spreading and positioning of the module is possible along the Y axis. The identity of the modular units improves the clarity of the overall system and simplifies servicing and the production of the systems overall.

Pressure sensor technology is preferably integrated in the sliding carriage. This means that there is no need for hose connections between the pipetting tips and the pressure sensors, the flexibility of such hose connections impairing the precision of the pressure sensor technology. At the same time, the signal quality is increased and the response time of the pressure sensor is reduced by means of the direct coupling of the sensor.

Where required, it is possible to integrate a barometric liquid level detection (LLD). In this case it is possible to use the pumps that have already been integrated to generate dynamic pressure in a controlled manner. On account of the overall lower dead volume in the system, the response times for the barometric LLD are better than those for systems with hose systems leading to external pumps.

Further advantages are produced from the additional claims and the following description.

BRIEF DESCRIPTION OF THE FIGURES

The invention is described in more detail below by way of embodiments that are represented in the Figures. In which.

DETAILED DESCRIPTION OF PREFERRED EMBODIMENTS

The invention is now described in more detail with reference to the attached drawings. The embodiments, however, are only examples that are not to restrict the inventive concept to a specific arrangement.

Before the invention is described in detail, it must be pointed out that it is not restricted to the respective components of the apparatus and the respective method steps, as the said components and methods can vary. The terms used in this case are purely used to describe particular specific embodiments and are not used in a restrictive manner. In addition, if in the description or in the claims the singular or non-specific articles are used, this also refers to the plural of the said elements unless the overall context specifically makes clear something to the contrary.

The Figures show a positioning device for positioning pipettes 10 of a pipetting apparatus, more especially for aspirating and dispensing processes in the medical-technical area, wherein in a profiled rail 21, which preferably forms or bears the toothed rack profile 26, the pipetting apparatus is accommodated or respectively integrated as extensively as possible in the toothed rack of the pipetting system. Thus, it is possible to aspire liquids internally of the pipetting system in a precise, reproducible and monitored manner at one site and then to dispense them to another site.

Figure 1:
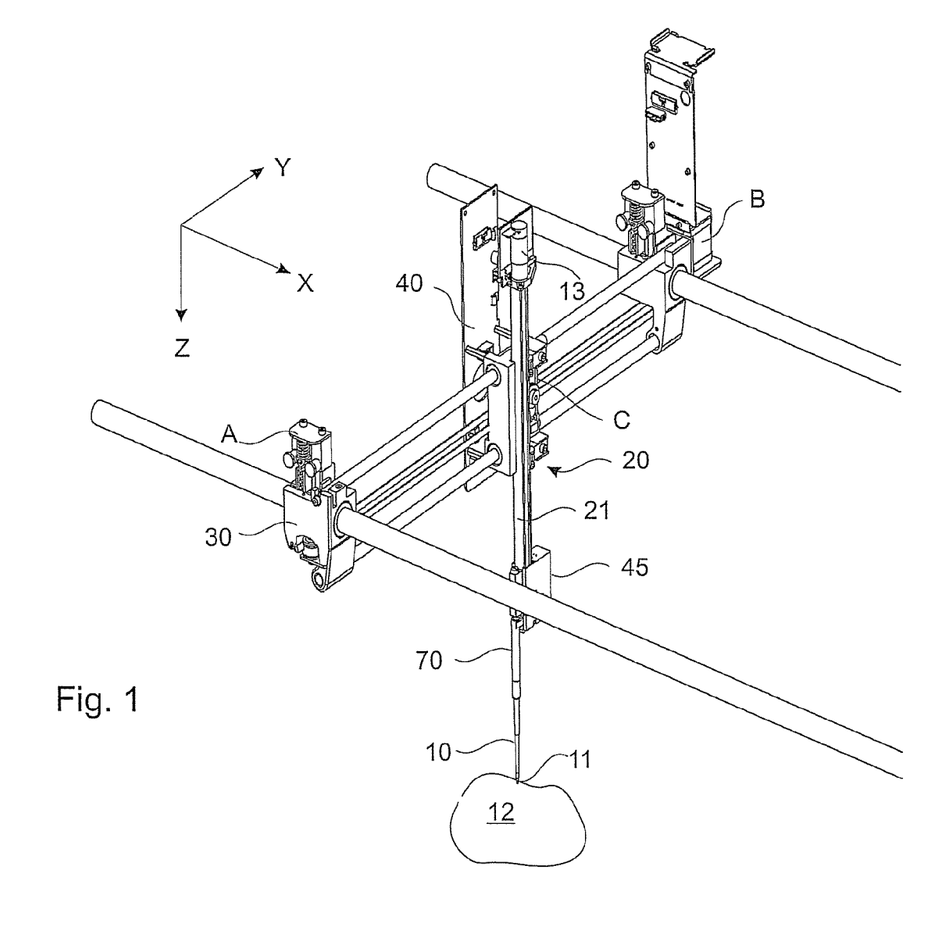
FIG. 1 is a view of a positioning device for a pipetting system.

FIG. 1 shows the positioning device with three drive units A, B, C as main drives for three sliding carriages 30, 40, 20. The drive unit A drives a first sliding carriage 30 in a first horizontal direction X. The second drive unit B is disposed on the first sliding carriage to move a second sliding carriage 40 in a second horizontal direction X, which is preferably at right angles to the first horizontal direction X. The drive unit C is provided on the second sliding carriage 40 to move the third sliding carriage 20 in a vertical direction Z, the sliding carriage 20 being moveable transversely, preferably at right angles to the working area. This embodiment corresponds to a movement within a Cartesian system of coordinates, it being possible to control the sliding carriages independently of each other. However, the three directions X, Y, and Z have not to be arranged at right angles, thus, other arrangements being possible as long as the third sliding carriage 20 can be moved transversely to and away from the working area.

Figure 2:
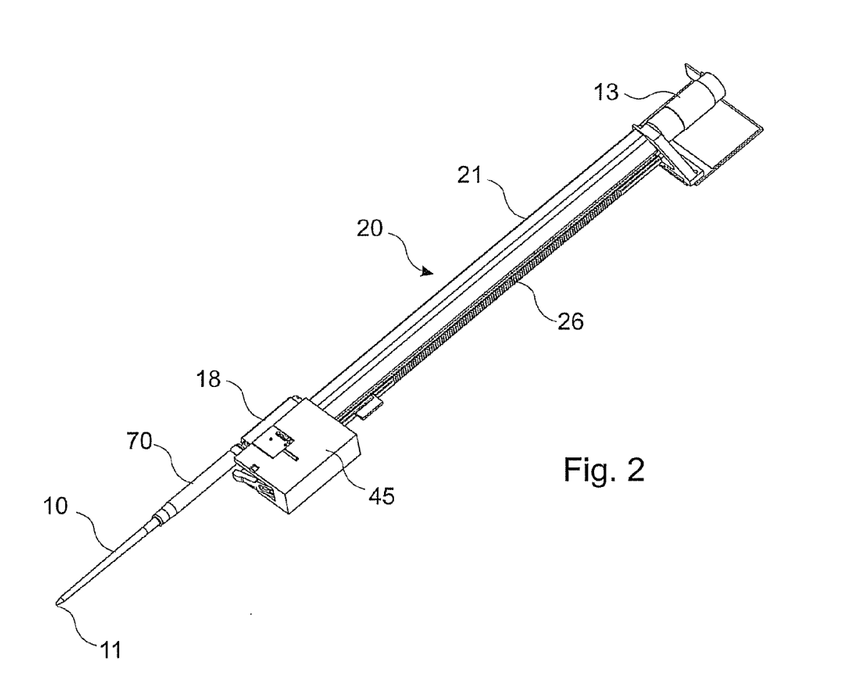
FIG. 2 is a view of the pipetting system.

FIG. 2 shows the sliding carriage C 20 that at the same time forms the pipetting apparatus. As such, the pipetting apparatus is accommodated in the positioning device with at least one, where required removable pipette 10 or respectively pipetting tip 11. In principle, the drive units A, B, C work to position the pipette or respectively the pipetting tip by moving the same in, where applicable, several directions X, Y over a working area 12 and in a direction Z transversely to the working area 12. The said directions do not have to be horizontal or vertical as shown in the exemplified embodiment or do not even have to form a Cartesian system of coordinates, the sole certainty is that, where required, it is possible to home in on a specific point that lies within the system with the tip of the pipette.

The pipette 10 or respectively the pipette tip 11 is secured in a detachable manner to the third sliding carriage 20 that is moveable transversely to the working area 12. At least one pump drive 13 with at least one pump 14 and at least one pump chamber 15, 16 is provided to carry out the aspirating and/or dispensing process. In addition, a control unit is provided to control at least the drive units A, B, C and the pump drive 13 in conjunction with the associated measuring device.

Figure 3:
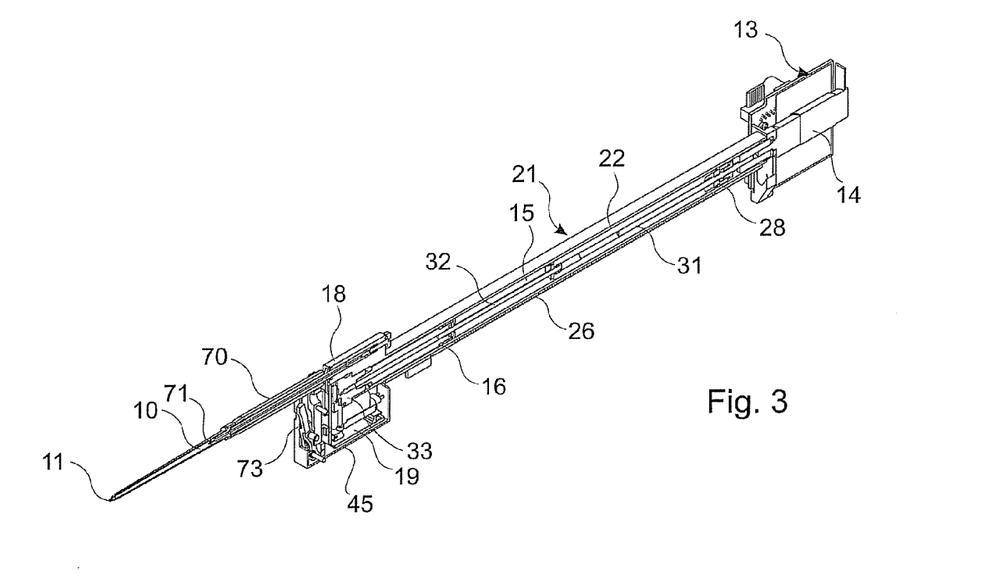
FIG. 3 is a three-dimensional sectional representation through the pipetting system.
Figure 4:
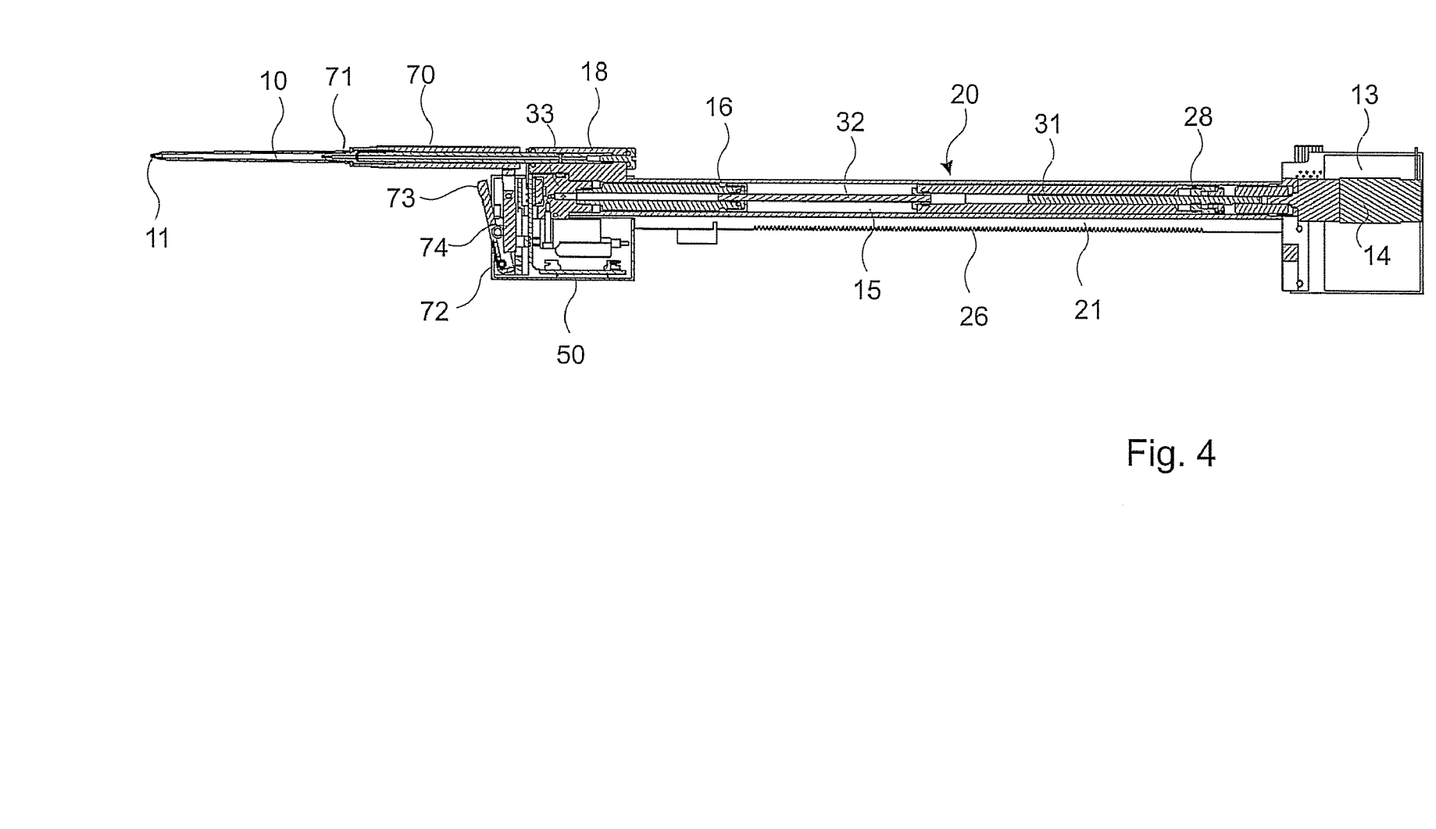
FIG. 4 is a sectional representation through the pipetting system.

According to FIGS. 3 and 4 the at least one pump drive 13 comprising pump 14 and at least one pump chamber 15, 16 is provided in the sliding carriage 20 that is moveable at right angles to the working area 12 and is accommodated by the sliding carriage 20 and integrated in the sliding carriage. In principle only one pump chamber 15 can be used, in the embodiment, however, several pump chambers 15, 16 with different volumes are provided.

Figure 7:
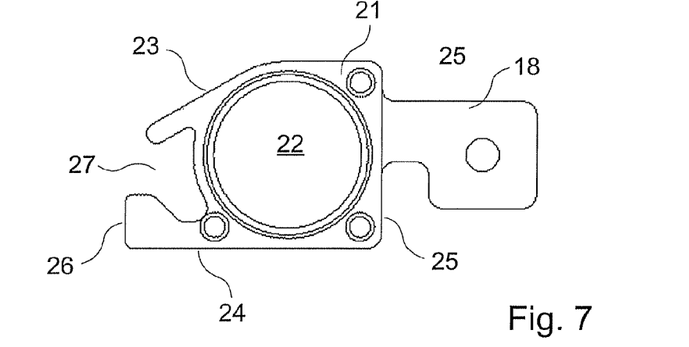
FIG. 7 is a section through a profiled rail that is disposed in the Z axis.

The sliding carriage 20 is formed by a profiled rail 21 with, as shown in FIG. 7, at least one hollow space 22 in which additional components such as, for example, the pump drive 13 and the pump chambers are accommodated. In addition, the profiled rail 21 includes a toothed rack profile 26, an adapting region 18 for adapting the pipetting tip 11 and a cable duct 27. The adapting region 18 is consequently accommodated directly on the profiled rail 21, critical mechanical tolerances thereby being omitted and the linearity between toothed rack and adapter tube being reproducible and easier to maintain. This means that there is no need for transitions that are difficult to adjust and can result in errors, mechanical damage and impairments in precision.

Figure 8:
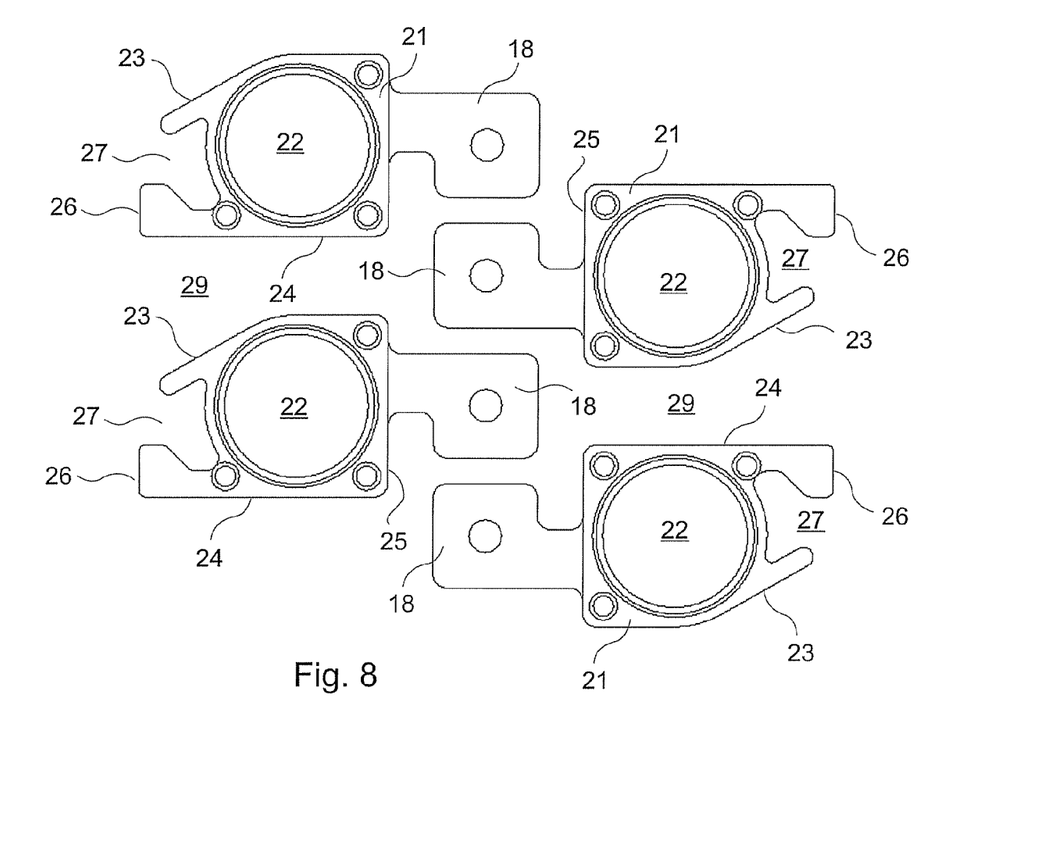
FIG. 8 is a section through a multiple arrangement of rails which is disposed in the Z axis.

The adapting region 18 of the profiled rail 21 and the toothed rack profile 26 as well as, where applicable, the cable duct 27 are disposed in such a manner at the profile between the three sliding faces 23, 24, 25 that the adapting region 18 and the toothed rack profile 26, where applicable with the cable duct 27, are situated diametrically opposite each other. This means that the prerequisite for the multiple arrangement represented in FIG. 8 is provided, which makes it possible on one hand in the case of a multiple arrangement for adjacent profiled rails only having to be rotated by 180 degrees one relative to another, and on the other hand, however, provides a guide means for the individual modular units in the intermediate spaces 29. The geometry of the profiled rail 21 makes it possible, with reciprocal disposing, to connect the systems together for example in a 9 mm grid enabling to use the remaining intermediate space 29 between the profiles for the individual bearing arrangement of the individual profiled rails. Other grid spacings are obviously possible.

The apparatus preferably includes the following fundamental elements:
- a profiled rail 21 with toothed rack profile 26 with a 3-face bearing concept
- receiving and releasing mechanism for DiTi (disposable tips)
- a DiTi detection sensor for controlling its presence
- a pump drive 13 with pump 14 and pump plunger drive with initializing sensor, position control and monitoring
- at least one pump chamber 15, 16 for mono or dual operation
- valves for selecting the pump chamber, ventilation, etc.
- pressure sensor for monitoring the system pressure, monitoring the aspiring process
- barometric liquid level detection
- capacitive liquid level detection
- facility to connect together to form multiple needle arrangements
- integrated digital signal processing
- integrated Z and Y drive in the case of multiple needle modules.

This system is used in place of toothed racks that are conventionally moved in a vertical manner and is preferably moved in three directions X, Y, Z using conventional drive technology. A profiled rail 21 offering corresponding guide faces and drive interfaces (teeth) is used for the Z movement. Drive unit C for the movement in the Z direction and the associated sensor technology are components of the Y axis modules, that-is-to-say of the sliding carriage 40.

The systems can also be connected together to form multiple needle arrangements. In this case, each module includes a sliding carriage 40 with autonomous drive units B, C for movement in the Y and Z directions. This means that it is possible to construct multiple duct pipetting systems of an arbitrary number. A substantial advantage when using the system is that the systems disposed in the third sliding carriage 20 moveable transversely to the working area are integrated there as extensively as possible, which means that there is no need for hose connections to external pumps, pressure sensors and the like. This considerably simplifies the design and complexity of the overall pipetting system especially in the case of multiple arrangements.

To this end the third sliding carriage 20 that is formed by the profiled rail 21 forms a module that is closed as extensively as possible, having only few interfaces to the outside. The toothed rack profile 26 provides the mechanical interface to the pipetting system (with first sliding carriage 30 moveable in X direction and second sliding carriage 40 moveable in Y direction); a foil strip cable for example can provide the electrical connection, other electrical connections also being possible. This means that the system on account of the few and clearly definable interfaces exhibits good characteristics for integration in diverse pipetting systems.

The profiled rail 21 used preferably as the third sliding carriage 20 is moved in the Z direction and consequently mostly in a vertical manner. If consequently the terms "top" and "bottom" are used below, this refers to the arrangement along the vertical Z axis even if other arrangements are conceivable. The profiled rail 21 has at its top end an interface to the pump drive 13, at its bottom end an adapting region 18 for adapting pipetting needles as well as an interface to the sensor head 45.

The profiled rail 21 forms the central component and its special geometry enables at least a part of the following functions, that is
- the system bearing arrangement at the first sliding carriage 30 moveable in the X direction, and/or the second sliding carriage 40 moveable in the Y direction by means of play-free pre-stressed sliding bearings,
- the drive of the profiled rail through the intermediary of the toothed rack profile 26,
- the accommodating of the pump chambers 15, 16 and the pump drive in the interior of the profile,
- the accommodating and securing of connecting cables in a cable duct 27,
- the facility to connect the system together with a spacing between needles of, for example, 9 mm.

Figure 9:
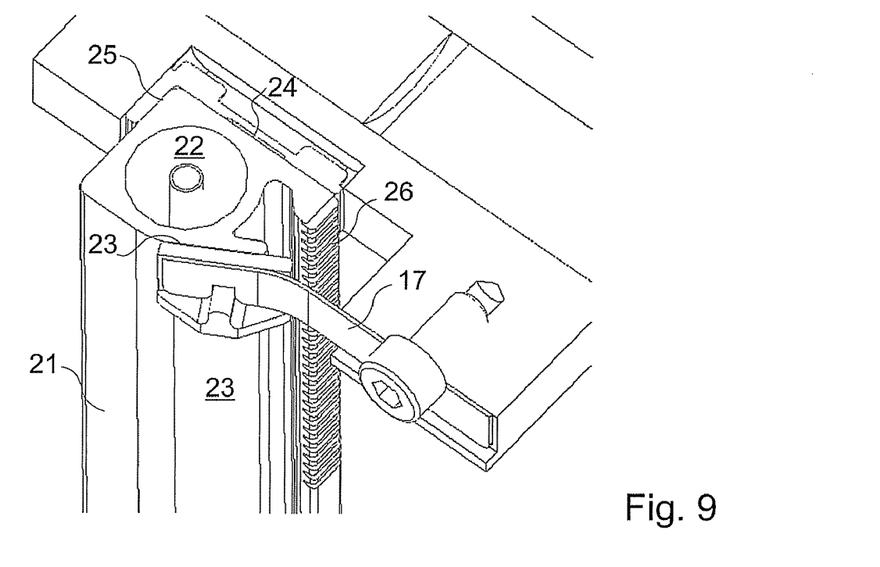
FIGS. 9, 10 are schematic representations of the bearing arrangement of the profiled rail.
Figure 10:
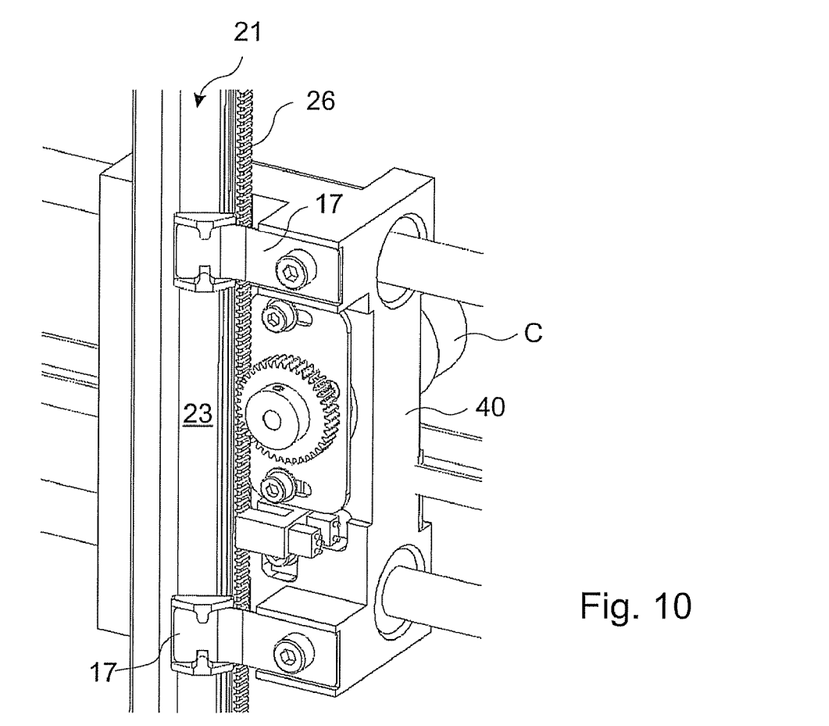

The profiled rail bearing arrangement according to FIGS. 9 and 10 is based on a 3-face sliding bearing in two planes, wherein according to FIG. 9 one sliding bearing face 23 is initially biased in a spring-loaded manner by means of a spring 17 against the other two sliding bearing faces 24, 25. This produces the following characteristics that are in part known from WO 2005/010383 A1:
- the bearing arrangement is free from backlash in the X and Y directions and rotationally relative to the Z axis,
- on account of the bearing friction the profiled rail 21 that forms the third sliding carriage 20 remains in its last position with the drive unit C in the currentless state. Consequently, it is not possible for the sliding carriages to fall onto the working area 12 into the specimen containers etc. that are located underneath and cause contamination
- on account of the bearing friction the play between the toothed rack and the driving toothed wheel is clearly defined (that-is-to-say the tooth flanks are always applied in the direction of rotation). This is important for the positioning of the system in the Z direction (minimum dead volume in specimen containers)
- the systems can be displaced by hand which is important for servicing, that-is-to-say the drive has no self-locking.

By changing the length of the profiled rail 21, systems with different Z travel paths can be realized and can consequently be adapted to the respective application.

In the region of the sensor head 45 there is provided an apparatus that checks whether a disposable tip has been picked up, is present or has been discharged. To this end a discharging mechanism is integrated in the sensor head. In addition there is provided a displacement sleeve 70 for detecting and discharging the disposable tip. A picking-up adapter 71 seals the disposable tip in a gas-tight manner, the volume of air in the pipette being connected to the pipetting device by means of an inside bore.

Figure 5:
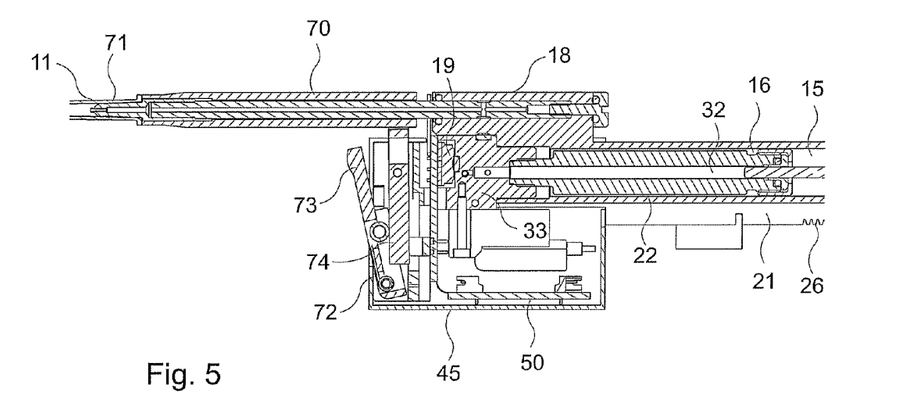
FIG. 5 is a sectional representation through the sensor head of the pipetting system.
Figure 6:
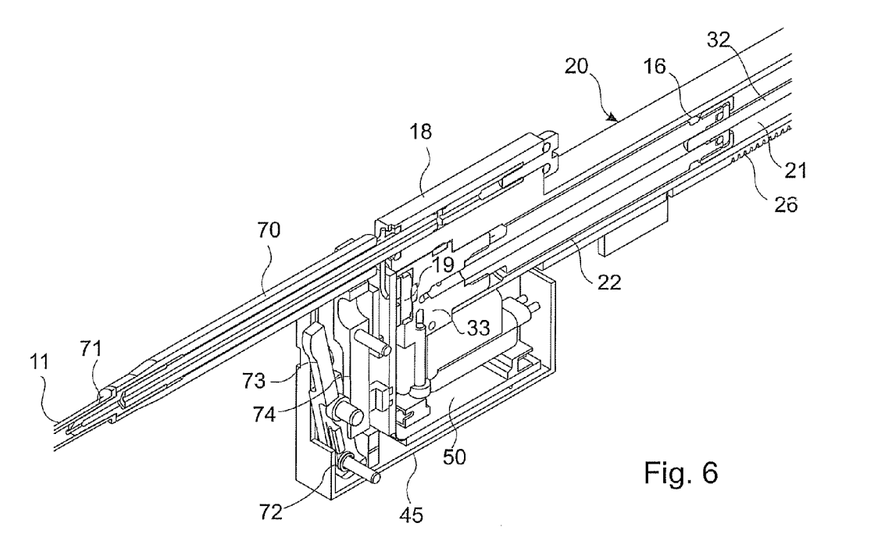
FIG. 6 is a three-dimensional sectional representation through the sensor head of the pipetting system.

FIGS. 5 and 6 show the discharging mechanism, which includes a first lever 73 that is mounted in opposition to the force of a spring 72 and, when a disposable tip is in position, that-is-to-say when the adapter sleeve 70 abuts against the sensor head 45, stands out from the sensor head as in FIGS. 5 and 6. This lever interacts with an additional lever 74 such that when the disposable tip has been discharged it interrupts a photoelectric barrier, which indicates that the pipette tip 11 has been discharged. Other sensor possibilities are possible for detecting the presence of the disposable tip and for determining the discharge.

In the pump drive 13 there is provided a pump, which is formed by a spindle drive. A rotating spindle nut drives a spindle as the pump plunger, which then works as a piston in the pump chamber. The pump drive comprises a drive (for example a DC geared motor with encoder for positioning control, a stepping motor or the like) which drives a spindle. By means of the spindle nut, which is low in backlash and is optimized to the spindle, an adapter sleeve 28 is moved and positioned in a linear manner in the profiled rail 21, the positioning control, the spindle accuracy, etc contributing to the precision of the pipetting system. This adapter sleeve can be modified or exchanged for adapting the length in order to accommodate for example other pump plungers.

The system can be operated as a mono system with only one pump chamber or as shown in the embodiment of FIG. 3 it can be operated with up to several pump chambers, in this case two pump chambers 15, 16 as a dual system.

In the case of a mono system one pump chamber 15 is situated in the profiled rail 21. The pump chamber is adapted in a valve disk 33 and is sealed with a seal so as to be gas-tight against the pump plunger 32. By the displacement of the pump plunger following the rotation of the spindle nut that is retained axially in the direction Z, air in the pump chamber is displaced into the valve disk 33 or is sucked-in. The displaceable volume of the pump chamber can be adapted to the respective application by adapting the diameter of the pump plunger and the useful length of the pump plunger. So systems for pipetting processes from the µl range to the ml range can be realized by adapting the volume of the pump chamber. The overall modular design of the pump chambers makes them simple to change.

In the case of a dual system, two pump chambers 15, 16 are disposed one behind the other in the third sliding carriage 20 and are used in common by the pump drive. The bottom pump chamber 16 for small pipetting volumes is directly adapted in the valve disk 33 and is sealed in a gas-tight manner with a seal against the bottom pump plunger 32 (identical to the mono system). The top pump chamber 15 for large pipetting volumes is also connected in a gas-tight manner to the valve disk 33. Displaced air from the top pump chamber is conducted outwards to the bottom pump chamber 16 and is also introduced into the valve disk 33. Through the displacement of the two mechanically coupled pump plungers 31, 32, air is displaced out of the pump chambers into the valve disk 33 or is sucked in. The mechanical coupling can for example be developed such that the two pump plungers are driven in common by the pump drive 13, their effect, however, being influenced by the valve disk 33 by one or none of the pump chambers 15, 16 being ventilated via the ventilating line. In this case too, the displaceable volume of the pump chamber can be adapted to the respective application by adapting the diameter of the pump plunger and adapting the useful length of the pump plunger. An adaptation between the dual and the mono system can be effected for example by means of the adapter sleeve 28.

This arrangement allows two pipetting volumes to be realized internally of one system, such that the most suitable pump chamber for the respectively desired pipetting volume can be selected in order to obtain optimum pipetting precision. Consequently, the system can be used at the same time both in the µl range and in the ml range.

Through the intermediary of the valve disk 33, all the necessary connections between the pump chambers 15, 16—both in the mono system and the dual system or also in the case of multiple chamber systems—are realized by means of valves for selecting the pump chambers, for ventilating and for connecting to the pipetting needle 11 and to the pressure sensor technology 19 or to alternative sensors such as flow rate sensors. Depending on the desired application (mono system, dual system; application options) it is possible to adapt the internal structure of the valve disk 33. The external mechanical interfaces, on the other hand, to the pump chambers 15, 16, to the toothed rack profile 26, to the adapter for the pipetting needle and to the valves, etc. remain unchanged. The design of the systems, consequently, is modular and flexible. A substantial advantage of the construction is the hose-free design and related thereto the drastic reduction in sealing points. At the same time, the severe reduction in the dead volumes in the system contributes to an increase in the precision of the pipetting system.

Two 3/2-way solenoid valves are provided in the valve disk for switching the possible air paths. The valve disk 33 is connected to the pump chamber by means of an interface and in addition has a connection to the adapter region 18, a ventilating valve and a connection to the pressure sensor technology 19.

With the above-mentioned options of the valve disk 33 and the components there are different application possibilities which can result in various pneumatic circuits that are also familiar to the man skilled in the art. Mono systems with system ventilation are possible, with or without a ventilating function of the disposable tip, one or more valves being used depending on the design. In the case of dual systems, it is also possible to have such with ventilation and without ventilation of the disposable tip. In the case of a construction with for example two pump chambers 15, 16, up to three 3/2-way valves can be necessary. In the case of this embodiment the piston volume can be selected by means of valves to expand the pipetting volume range. Formation of bubbles at the disposable tip is avoided with the LLD search by separate ventilation of the disposable tip. The pistons are separate from the disposable tip when repositioning after the LLD. This means that there is no risk of bubble formation at the disposable tip when repositioning. The pistons and also the disposable tip can be ventilated separately from one another. This produces an operationally secure system.

A Pressure sensor technology 10 associated with the valve disk 33 can be disposed in the region of the sensor head 45. This pressure sensor can measure for example the differential pressure between the inside pressure of the pipette and the surrounding air pressure. When the system is operating, the pressure sensor signal can be used for various functions such as for example the monitoring of the system for inadmissible pressure ranges, self-diagnoses and system leakages. However, a barometric liquid level detection (LLD) or a verification of the aspirating and/or dispensing process can also be carried out by evaluating the pressure curves.

The barometric liquid level detection is based on a measurement of the dynamic pressure of the air emitted from the pipetting tip 11 or of the air sucked-in to the pipetting tip 11. As soon as the pipetting tip 11 contacts the surface of a liquid, the inside pressure in the pipetting tip changes. On recognition of the said pressure change the Z ordinates of the pipetting apparatus are defined and consequently the position of the surface of the liquid is determined.

It is also possible to have a capacitive liquid level detection (LLD) at the sensor head 45 as an alternative to or separate from the barometric LLD. The needle tube is electrically insulated for this purpose and a contact spring is provided for capacitive LLD sensor technology. The capacitive liquid level detection is based on a measurement of the change in electric capacity between the device mass and the pipetting tip 11 or respectively the end of the disposable tip. As soon as the pipetting tip contacts the surface of a liquid, the capacity changes accordingly. On recognition of the said change in capacity, the Z ordinates of the Z axis of the pipetting apparatus are defined and consequently the position of the surface of the liquid is determined. It is necessary for this method that the metal needle tube with the adapter tip is accommodated electrically insulated in the profiled rail 21. The disposable tip also has to be conductive in order to be able to measure the change in electric capacity. The combination of the capacitive and the barometric LLD produces a very reliable pipetting system.

As an alternative or in addition, a flow rate sensor can also be provided at the sensor head. The volume of air flowing past can be quantified using a flow rate sensor of this type, for example by means of thermo-anemometers.

Each modular unit in the form of the sliding carriage 20 with associated pump drive 13 and additional components has its own control unit 50 and consequently also signal processing unit for processing the sensor signals directly at the measured value sensing element. This greatly simplifies the integration of the module into pipetting systems because the higher-ranking system does not have to provide interfaces, etc for this. In addition, the processing time of the signals can be reduced, which means that the pipetting apparatus can react rapidly and flexibly to the sensor signals.

In spite of the high degree of integration of the components necessary for the pipetting process in the third sliding carriage 20, the system provides good possibilities for adapting the systems to the most varied applications. The modular design of the pump chamber(s) 15, 16 allows to adapt to different pipetting volumes. In this case internally defined interfaces are created and these guarantee the compatibility of the pump chambers one with another. The valve disk 33 also provides a plurality of possible application options, which have no effects mechanically on the system whatsoever with regard to given mechanical conditions. Internally defined interfaces create the modularity in this case. An adaptation of the system with regard to the travel that can be realized can be achieved by means of simple adaptation of a few parts (toothed rack, spindle adapter).

On account of not having any external hose connections and the reduction of electrical connections down to one foil strip cable, integration in pipetting systems is simplified in a substantial manner. The simple and nevertheless robust bearing concept can easily be rearranged and also connected together to form multiple needle systems. Electrically speaking, only one foil strip cable is required externally for the connection. The module is supplied with operating voltage by means of this foil strip cable. Communication is carried out by means of a CAN interface. Irrespective of the position of the system in the overall device, the module can be addressed as a CAN module. This simplifies, standardizes and modularizes the design of complex pipetting systems.

Figures 11, 12:
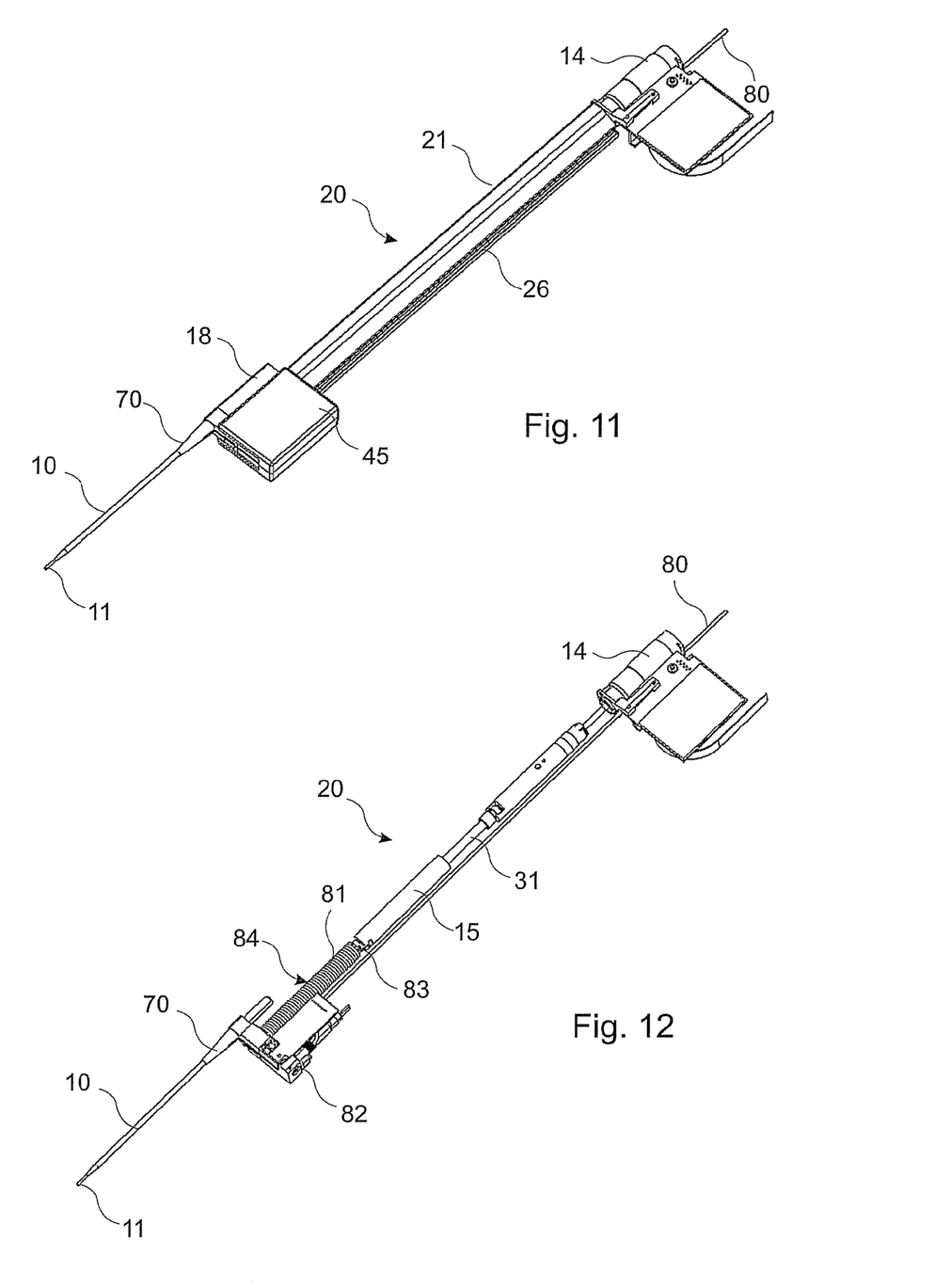
FIG. 11 is a view of a further embodiment of the pipetting system.
FIG. 12 is a view as in FIG. 11 without profiled rail.

Gases or liquids can be used as the system medium, that-is-to-say as the medium with which the pump sucks in the liquid (the medium) to be picked up. The embodiment in FIGS. 1 to 10 is designed to use air as the system medium, however, in the embodiment shown in FIGS. 11 and 12 it is also possible to use a liquid as the system medium. In this case it must be ensured that the pump chambers and the pump do not become contaminated and that a flushing liquid can be used, which does result in structural changes even if the exterior appearance is substantially unchanged. The view shown in FIG. 11, consequently, is extensively identical to the representation in FIG. 2 even though the use of a flushing line 80 for the flushing liquid is provided. The pipetting volume is accommodated completely in one pipetting hose 81, since an entry into the pump 14 for the medium to be aspired is not an option. This means that the pump chamber is replaced at least partially by the pipetting hose 81, which is simple to clean and is integrated in the profiled rail.

It is also very important for the precision of the device in this case that the pump 14 is integrated in the sliding carriage and that fixed, hose-free connections are preferably provided in the region of the system liquid. The additional flushing pump, which is connected to the flushing line 80 and is not represented in the drawing, can be integrated in the sliding carriage but does not have to be; at the same time the flushing pump and the flushing line have no influence on the pipetting quality. They can be actuated from externally and the flushing pump can preferably be disposed on the sliding carriage 40.

The changeover between flushing and dosing is carried out by means of an integrated valve. As the pump chamber 15 can be filled by means of two openings, a simple 2/2-way valve, with which the flushing pump is separated from the dosing pump (pump chamber) in the pipetting operation, will suffice. In the flushing operation, the fact that there is a separate inlet and outlet to the pump chamber guarantees that no air can remain in the pump chamber. When the entire system is flushed through, the pump chambers are also flushed through.

The pipetting hose 81 is generally guided from the needle tip to the pump chamber interface and can be wound in the form of a spiral with a hose volume of, for example, up to 1 ml. It can accommodate the entire pipetting volume. This guarantees that the specimen cannot be sucked in as far as the pump chamber. Systems with smaller pipetting volumes can be adapted by reducing the wound length of the pipetting hose. This is a great advantage compared to nowadays systems with external dosing pumps, for in that case the hose length and consequently the volume was determined by the travel of the pipetting mechanisms (up to 2 ml).

The pipetting tip is part of a module 84 which including the pipetting hose 81 is removable from the device and has an interface 82 to the valve module and an interface 83 to the pump chamber. In this case too, it is possible to provide a plurality of pump chambers by using suitable valves.

It is obvious that this description can be subject to the most varied modifications, changes and adaptations, which are to be considered as equivalents to the attached claims.

The invention claimed is:

1. Positioning device for positioning pipettes for aspirating and/or dispensing of media in medical-technical applications, the said device comprising
    at least one pipetting apparatus with at least one pipette tip of the pipette,
    a plurality of drive units for positioning the pipette tip and for moving the pipette tip in at least one direction over a working area and in a direction transversely to the working area towards the working area or away from the working area,
    at least one sliding carriage that is moveable in the direction transversely to the working area, the pipette tip being secured in a detachable manner to the sliding carriage,
    at least one pump drive comprising at least one pump and at least one pump chamber for aspirating and/or dispensing of a medium,
    a control unit for controlling at least the drive units and the pump drive in conjunction with associated measuring devices,
    wherein the sliding carriage that is movable transversely to the working area is formed by a profiled rail with at least one hollow space extending in a longitudinal direction of the profiled rail, wherein the at least one pump drive together with the pump and the at least one pump chamber is accommodated by the at least one hollow space and is integrated in the hollow space, and wherein the control unit for controlling the pump drive in conjunction with associated measuring devices is integrated in the at least one sliding carriage that is movable transversely to the working area.

2. Device according to claim 1, wherein the at least one pipette tip is removable and a part of the pipette that is removable.

3. Device according to claim 1, wherein a plurality of pump chambers with different volumes are provided in the sliding carriage.

4. Device according to claim 1, wherein two pump chambers are disposed one behind the other in the sliding carriage, wherein, when the pump drive is actuated, air displaced in one pump chamber is conducted around the other pump chamber in the sliding carriage.

5. Device according to claim 1, wherein the sliding carriage is mounted in two planes by means of a 3-face sliding bearing comprising three sliding bearing faces, wherein one sliding bearing face is initially biased against the other two sliding faces by means of a spring.

6. Device according to claim 1, wherein the profiled rail comprises at least one of a toothed rack profile, a cable duct, and an adapting region for adapting the pipetting tip.

7. Device according to claim 6, wherein at least two of the elements comprising the adapting region for adapting the pipetting tip, the toothed rack profile or the cable duct are disposed between three sliding bearing faces and are situated opposite one another diametrically.

8. Device according to claim 7, wherein the adapting region and the toothed rack profile together with the cable duct are situated opposite one another diametrically.

9. Device according to claim 1, wherein a plurality of profiled rails is adapted to be connected together for developing multiple needle systems.

10. Device according to claim 9, wherein consecutive juxtaposed profiled rails are rotated by 180 degrees one relative to another in profile cross-section.

11. Device according to claim 1, wherein the pump drive is a spindle drive, via which an adapter sleeve drives at least one pump plunger as a piston internally of the at least one pump chamber.

12. Device according to claim 11, wherein a plurality of pump chambers are provided, each of which comprising a pump plunger, wherein these pump plungers associated with the pump chambers are coupled in a mechanical manner.

13. Device according to claim 1, wherein a pressure sensor technology is disposed at the sliding carriage.

14. Device according to claim 1, wherein a valve disk is provided at the at least one sliding carriage, the valve disk being connected to the at least one pump chamber and to a pressure sensor technology.

15. Device according to claim 1, wherein at least one of a barometric or a capacitive liquid level detection is provided at the at least one sliding carriage.

16. Device according to claim 1, wherein the positioning device includes three drive units as main drives, one of which drives a first sliding carriage in a first horizontal direction, on which sliding carriage the second drive unit is disposed for moving a second sliding carriage in a second horizontal direction, which is preferably at right angles to the first horizontal direction, wherein the drive unit for moving the third sliding carriage in a vertical direction is provided on the second sliding carriage, wherein the sliding carriage is moveable at right angles to the working area.

17. Device according to claim 1, wherein the pump moves a system medium that is a liquid.

18. Device according to claim 1, wherein there is provided a pipetting hose, which is generally guided from a pipetting tip to a pump chamber interface.

19. Device according to claim 18, wherein the pipetting hose is integrated in the sliding carriage wound in the form of a spiral.

* * * * *